(12) United States Patent
Zinnanti

(10) Patent No.: US 9,968,340 B2
(45) Date of Patent: May 15, 2018

(54) BIOPSY DEVICE WITH AUTOMATIC ASPIRATION

(71) Applicant: William Zinnanti, Santa Cruz, CA (US)

(72) Inventor: William Zinnanti, Santa Cruz, CA (US)

( * ) Notice: Subject to any disclaimer, the term of this patent is extended or adjusted under 35 U.S.C. 154(b) by 0 days. days.

(21) Appl. No.: 14/055,292

(22) Filed: Oct. 16, 2013

(65) Prior Publication Data
US 2014/0114210 A1     Apr. 24, 2014

Related U.S. Application Data

(60) Provisional application No. 61/717,745, filed on Oct. 24, 2012.

(51) Int. Cl.
| A61M 31/00 | (2006.01) |
| A61B 10/00 | (2006.01) |
| A61M 37/00 | (2006.01) |
| A61M 5/20  | (2006.01) |
| A61B 10/02 | (2006.01) |

(52) U.S. Cl.
CPC .. *A61B 10/0283* (2013.01); *A61B 2010/0208* (2013.01)

(58) Field of Classification Search
CPC ..................................... A61B 5/00
USPC ........ 600/562, 564, 565, 566, 567; 604/133, 604/135
See application file for complete search history.

(56) References Cited

U.S. PATENT DOCUMENTS

| 3,923,066 | A | * | 12/1975 | Francisoud | ........... A61M 25/04 604/170.01 |
| 4,231,367 | A | * | 11/1980 | Rash | ................. A61M 25/0014 604/165.02 |
| 4,500,312 | A | * | 2/1985 | McFarlane | ........ A61M 25/0631 604/192 |
| 4,573,981 | A | * | 3/1986 | McFarlane | ........ A61M 25/0631 604/192 |
| 4,601,708 | A | * | 7/1986 | Jordan | ..................... A61M 5/46 604/136 |
| 4,627,444 | A | * | 12/1986 | Brooker | ............. A61B 10/0045 600/571 |
| 4,641,663 | A | * | 2/1987 | Juhn | ...................... A61B 1/227 141/27 |
| 4,664,128 | A | * | 5/1987 | Lee | ............................... 600/566 |
| 4,713,057 | A | * | 12/1987 | Huttner | ............. A61M 25/0612 604/164.07 |
| 4,994,042 | A | * | 2/1991 | Vadher | .............. A61M 25/0631 604/110 |
| 5,069,224 | A | * | 12/1991 | Zinnanti, Jr. | ................. 600/565 |
| 5,159,933 | A | * | 11/1992 | Hut | .................... A61B 10/0283 600/566 |
| 5,186,712 | A | * | 2/1993 | Kelso | ................ A61M 25/0606 604/157 |

(Continued)

*Primary Examiner* — May Abouelela
(74) *Attorney, Agent, or Firm* — Cardinal Law Group

(57) ABSTRACT

The invention provides a disposable endometrial biopsy device comprising an elongated blunt-end catheter with distally placed tissue acquisition side-hole and proximally attached aspiration syringe with spring-loaded plunger having latching mechanism to release plunger for induction of aspiration. The device has a pin-hole channel or filter acting as a tissue trap between the catheter channel and the syringe in order to prevent aspiration of tissue into the body of the syringe.

4 Claims, 3 Drawing Sheets

(56) References Cited

U.S. PATENT DOCUMENTS

| | | | | |
|---|---|---|---|---|
| 5,217,024 A * | 6/1993 | Dorsey | A61B 10/0291 | |
| | | | 600/562 | |
| 5,281,206 A * | 1/1994 | Lopez | A61M 39/04 | |
| | | | 604/533 | |
| 5,316,013 A * | 5/1994 | Striebel, II | A61B 10/0275 | |
| | | | 24/606 | |
| 5,395,345 A * | 3/1995 | Gross | 604/187 | |
| 5,400,798 A * | 3/1995 | Baran | A61B 10/0275 | |
| | | | 600/567 | |
| 5,425,718 A * | 6/1995 | Tay | A61M 25/0643 | |
| | | | 604/158 | |
| 5,466,225 A * | 11/1995 | Davis | A61B 10/0283 | |
| | | | 600/567 | |
| 5,527,290 A * | 6/1996 | Zadini | A61M 5/158 | |
| | | | 604/157 | |
| 5,797,883 A * | 8/1998 | Prince | 604/170.01 | |
| 5,807,282 A * | 9/1998 | Fowler | 600/571 | |
| 5,971,939 A * | 10/1999 | DeSantis | A61B 10/0275 | |
| | | | 600/562 | |
| 6,042,552 A * | 3/2000 | Cornier | 600/562 | |
| 6,491,645 B1 * | 12/2002 | Gaber | 600/571 | |
| 7,207,950 B2 * | 4/2007 | Goldenberg | 600/562 | |
| 7,226,423 B2 * | 6/2007 | Goldenberg | 600/562 | |
| 7,390,306 B2 * | 6/2008 | Mark | 600/566 | |
| 7,458,940 B2 * | 12/2008 | Miller | 600/568 | |
| 8,043,316 B2 * | 10/2011 | Hardin | A61B 10/0233 | |
| | | | 600/562 | |
| 8,052,615 B2 * | 11/2011 | Reuber | A61B 10/0275 | |
| | | | 600/567 | |
| 8,070,691 B2 * | 12/2011 | Desilets et al. | 600/570 | |
| 2005/0113715 A1 * | 5/2005 | Schwindt et al. | 600/566 | |
| 2007/0106176 A1 * | 5/2007 | Mark et al. | 600/566 | |
| 2008/0294092 A1 * | 11/2008 | Mark | A61B 19/54 | |
| | | | 604/60 | |
| 2009/0192408 A1 * | 7/2009 | Mark | A61B 90/39 | |
| | | | 600/562 | |
| 2011/0208089 A1 * | 8/2011 | Sundheimer et al. | 600/567 | |
| 2012/0010527 A1 * | 1/2012 | Sundheimer et al. | 600/566 | |

\* cited by examiner

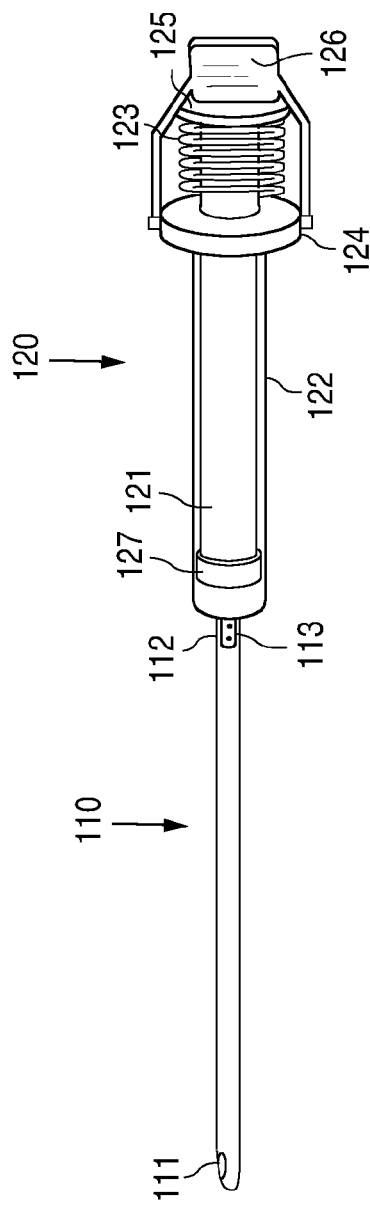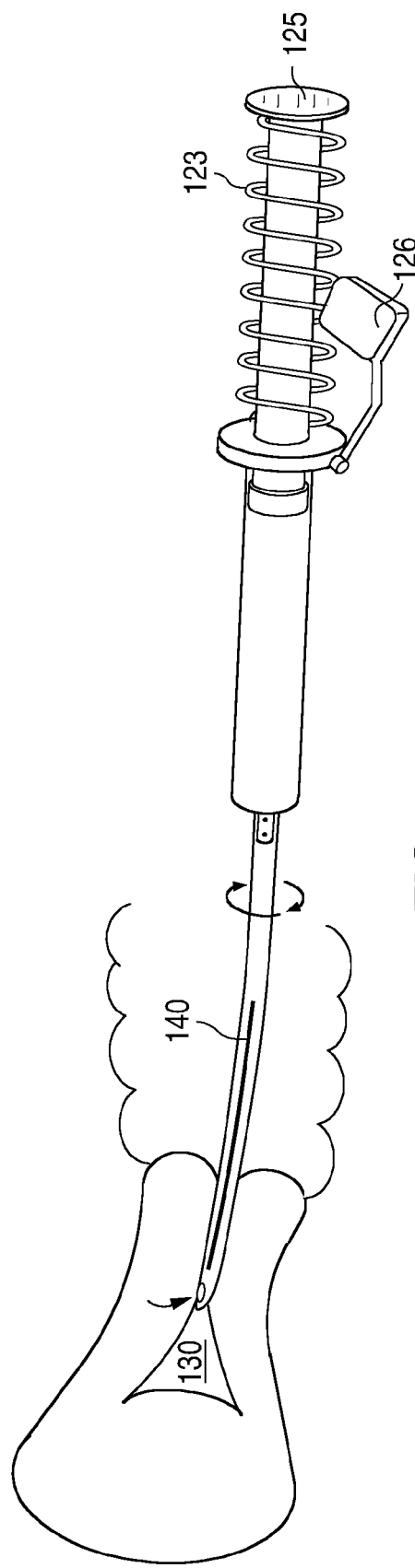
FIG. 1
FIG. 2

BIOPSY DEVICE WITH AUTOMATIC ASPIRATION

CROSS REFERENCE TO RELATED APPLICATION

This application claims the benefit of U.S. Provisional Application No. 61/717,745, filed Oct. 24, 2012, which is incorporated herein by reference in its entirety for all purposes.

TECHNICAL FIELD

This invention relates generally to surgical instruments. More particularly, the invention relates to a biopsy device that automatically creates suction to aspirate a specimen into the device.

BACKGROUND OF THE INVENTION

Routine endometrial biopsy is commonly performed using a flexible 3-mm catheter with rounded distal end having a side-hole for curettage and collection of tissue. Such catheters typically contain a flexible internal plunger that seals with the internal surface of the catheter. When the internal plunger is pulled back, suction is created. The suction is used to obtain endometrial tissue as the catheter is passed back and forth with rotation within the uterine cavity while the distal side hole scrapes tissue from the internal walls of the cavity. See, e.g., Zinnanti U.S. Pat. No. 5,069,224, Fowler U.S. Pat. No. 5,807,282, and Cornier U.S. Pat. No. 6,042,552.

The use of a flexible catheter follows the natural contours of the uterine cavity, which is an advantage to patient care, causing less pain and tissue trauma compared to needle or ridged-cannula biopsy devices. However, the process of transferring the sample from the catheter to a specimen container is inherently difficult with such typical biopsy devices because the flexible plunger must be reintroduced into the flexible catheter to expel the contents. This process is slow and technically difficult, and may result in loss of the sample, leading to the need for a second procedure.

Additionally, the limited volume of such typical endometrial catheters frequently does not create enough suction to obtain an adequate sample, and multiple passes with the same catheter, consisting of multiple iterations of obtaining and expelling a sample, must be performed. This process is further complicated by the need to prevent the sterile catheter tip from touching a non-sterile specimen container in order to prevent contamination when multiple passes are required.

Thus, although such prior-art devices can be simple to use and manufacture, each suffers from the disadvantages of a limited amount of suction and the need to force a long, flexible plunger back into the device in order to retrieve the specimen. These disadvantages result in loss of time and increased patient discomfort because the catheter must be reintroduced multiple times to retrieve an adequate sample and because the difficulty of replacing the plunger to retrieve the sample frequently leads to loss of sample, thus requiring a second procedure.

A few endometrial tissue collection systems employ the use of a syringe. The syringe has the advantage of creating more suction for aspiration so that an adequate sample is obtained each time; however, in currently available products, the plunger must be manually withdrawn from the syringe barrel to create suction. This action of pulling on the syringe plunger at the same time the catheter is inserted into the uterine cavity is inherently dangerous and may cause inadvertent harm or uterine perforation as the catheter is being pushed forward toward the patient and as the syringe is being pulled backward.

Spring-biased aspiration biopsy devices have been previously described by Lee U.S. Pat. No. 4,664,128, Hut U.S. Pat. No. 5,159,933 and DeSantis et al. U.S. Pat. No. 5,971,939 A. These devices have a variety of disadvantages based on the complicated grips, guides, and holders that encase the syringe and therefore introduce difficulty in retrieving the specimen if it is suctioned into the syringe. Indeed, the guides and holders described in Hut U.S. Pat. No. 5,159,933 and DeSantis et al. U.S. Pat. No. 5,971,939 A are in place to prevent overpressure from suctioning the tissue sample into the syringe.

Therefore, it would be desirable to provide an aspiration biopsy device that overcomes the aforementioned and other disadvantages.

SUMMARY OF THE INVENTION

One aspect of the present invention is an aspiration biopsy device. In one embodiment, the device is an endometrial biopsy catheter with proximally attached aspiration syringe having a pin-hole channel or filter acting as a tissue trap to prevent aspiration of tissue from the catheter into the syringe. In another embodiment, the biopsy device is an aspiration biopsy device with proximally attached syringe having spring-loaded plunger and latching mechanism to automatically create aspiration suction when the latch is released.

Another aspect of the present invention is a method of performing a biopsy procedure. In the method, an aspiration biopsy device is provided, the device comprising a catheter having a distally placed tissue acquisition side hole and a proximally attached syringe having a spring-loaded plunger and a latching mechanism. A distal portion of the device is inserted into a body cavity. Once the device portion is in place within the body cavity, the latching mechanism is manipulated to release the spring-loaded plunger, thereby automatically producing aspiration suction within the syringe. The device portion is moved in and out with a twirling motion, thereby collecting a biopsy sample via the distally placed tissue acquisition side hole. Once the biopsy sample is obtained, the device is removed and the sample is easily expelled by depressing the spring-loaded plunger with a thumb The aforementioned and other features and advantages of the invention will become further apparent from the following detailed description of the presently preferred embodiments, read in conjunction with the accompanying drawings, which are not to scale. The detailed description and drawings are merely illustrative of the invention, rather than limiting, the scope of the invention being defined by the appended claims and equivalents thereof.

BRIEF DESCRIPTION OF THE DRAWINGS

FIG. 1 is a perspective view of a biopsy device in accordance with the present invention;

FIG. 2 shows the device of FIG. 1 in position to obtain a tissue sample from a body cavity, a latching mechanism having been manipulated to allow expansion of the spring of a spring-loaded plunger, thereby automatically inducing aspiration of a sample into the device;

DETAILED DESCRIPTION OF THE PRESENTLY PREFERRED EMBODIMENTS

One aspect of the present invention is a biopsy device. In one embodiment, the device is an endometrial biopsy catheter with a proximally attached aspiration syringe, the catheter having a pin-hole channel or filter acting as a tissue trap to prevent aspiration of tissue from the catheter into the syringe. In another embodiment, the device is an aspiration biopsy device with a proximally attached syringe that has a spring-loaded plunger and a latching mechanism to automatically create aspiration suction when the latch is released. Devices in accordance with the present invention are illustrated in FIGS. 1-7.

FIG. 1 shows a biopsy device, in accordance with the present invention, ready for use. The device includes a catheter 110 (also referred to herein as an endometrial biopsy catheter) and a proximally attached syringe 120 (also referred to herein as an aspiration syringe). The term "catheter" is defined herein as an elongated, at least semi-flexible tube such as is illustrated in the figures. The term "syringe" is defined herein as a structure that comprises a hollow barrel fitted with a plunger, such as is illustrated in the figures. The term "proximal" (and its variants) refers to the portion of a device, or the portion of an element of the device, that is adjacent to the operator when the device is in use. The term "distal" (and its variants) refers to the portion of the device, or the portion of an element of the device, that is adjacent to the patient when the device is in use. In FIGS. 1 and 2, the distal end of the device is at the left and the proximal end of the device is at the right.

Figure 3:
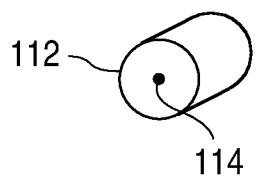
FIG. 3 is an enlarged view of a portion of the biopsy device of FIGS. 1 and 2, the enlarged view showing a tissue trap comprising a pin-hole channel.

As illustrated in FIG. 1, catheter 110 has a rounded distal end (i.e., the catheter has a blunt distal end) and includes a distally placed side hole 111 used for acquisition of a tissue sample into the interior or lumen of the catheter. Catheter 110 also includes a tissue trap 112 disposed in a proximal portion of the catheter that serves to prevent aspiration of biopsied tissue from the catheter into the aspiration syringe seen at 120. Tissue trap 112 may include either a filter 113, as illustrated in FIG. 1, or a pin-hole channel 114, as illustrated in FIG. 3.

Syringe 120 is proximally attached to catheter 110. I.e., syringe 120 is attached to a proximal portion of catheter 110. Syringe 120 may be attached to catheter 110 by any appropriate means, including, for example, the two elements being manufactured together to form an integral whole, the two elements being adhesively or otherwise bonded one to the other, or the two elements being snap-fit or otherwise mechanically connected one to the other.

Syringe 120 comprises a plunger 121 and a barrel 122. As seen in FIG. 1, plunger 121 is spring loaded, a spring 123 being held compressed between flange 124 of barrel 122 and the proximal end 125 of plunger 121 by a latching mechanism 126. The plunger proximal end serves as both a thumb (or finger) control portion of plunger 121 (i.e., the portion of the plunger to which typically a thumb is applied to depress the plunger, as seen in FIG. 7) and as a seat for latching mechanism 126 when the mechanism is latched to hold spring 123 in a compressed state as seen in FIG. 1.

When latching mechanism 126 is released from proximal end 125 of plunger 121, a distal portion of plunger 121 is automatically drawn through and partially out of barrel 122 by the expansion of spring 123, as seen in FIG. 2. Because plunger 121 includes a tip 127 that substantially seals with the interior wall of barrel 122, the withdrawing of plunger 121 in response to release of latching mechanism 126 automatically creates suction within barrel 122 that is communicated to catheter 110 via tissue trap 112. This suction is used to aspirate a tissue sample into the biopsy device through side hole 111. The aspirated tissue sample is prevented from entering syringe 120 and is maintained within the lumen of catheter 110 because, as is evident from, e.g., FIG. 1, barrel 122 is in communication with catheter 110 via tissue trap 112.

Operation of the device is illustrated, for example, in FIG. 2, which shows at least a portion of catheter 110 inserted into a uterine cavity 130. A tissue sample 140 has been aspirated into the lumen of catheter 110 through tissue acquisition side hole 111 (indicated by the curved arrow adjacent to the hole) as a result of releasing plunger 121 while catheter 110 is in place within the body cavity. Tissue acquisition is facilitated by moving catheter 110 in and out with a twirling motion during aspiration.

Figures 6, 7:
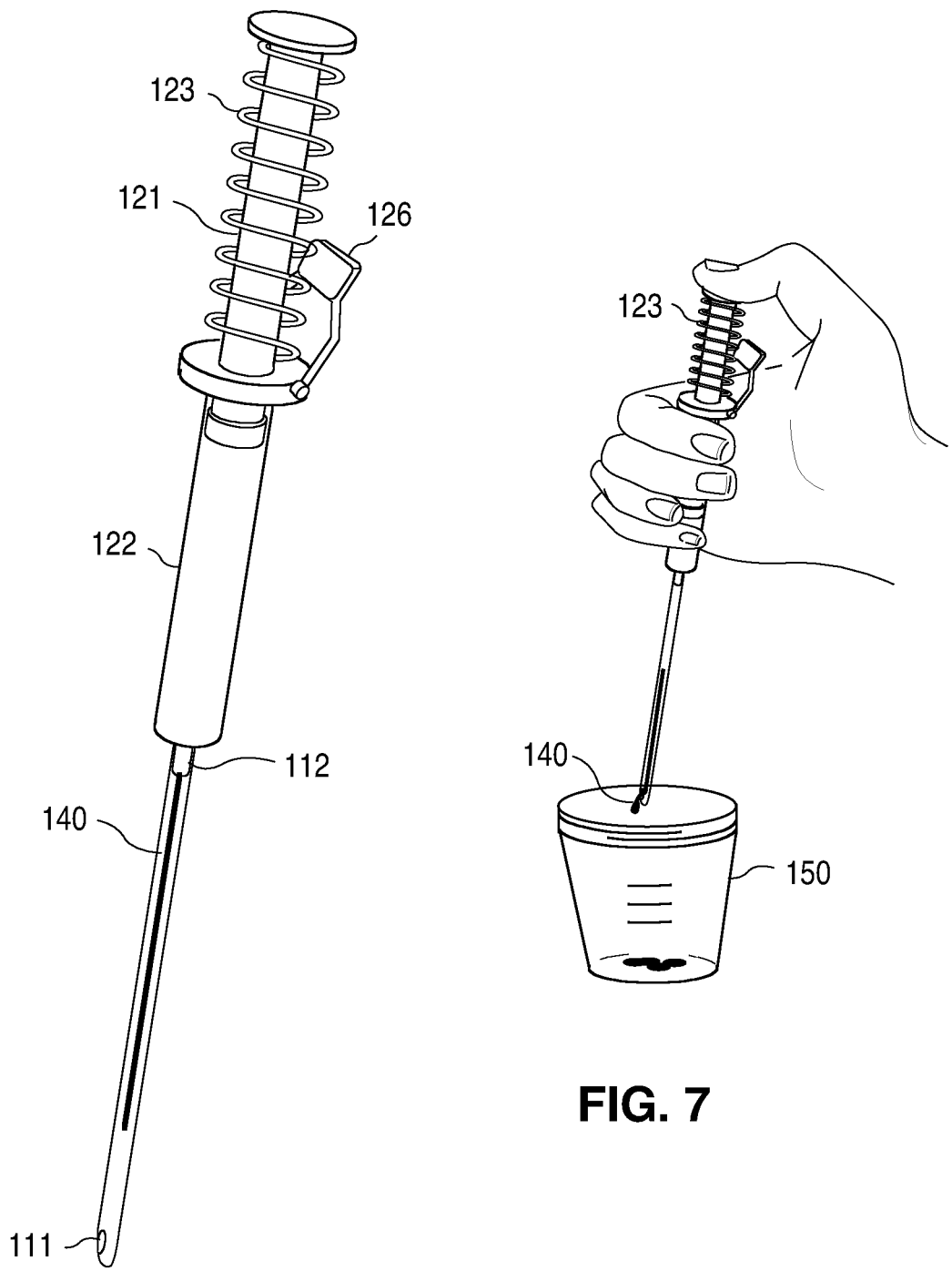
FIG. 6 is a perspective view of the biopsy device of FIGS. 1 and 2 with a biopsy sample disposed within the device.
FIG. 7 is a perspective view of the biopsy device of FIG. 6 being held adjacent to a specimen container as the biopsy sample disposed within the device is expelled into the specimen container.

FIG. 6 also shows a tissue sample 140 within the lumen of catheter 110. Syringe 120 may be sized to provide sufficient aspiration power to completely fill the lumen of catheter 110 with sample, thus avoiding the need for multiple passes with the device. Note that as seen in FIG. 6 tissue trap 112 has prevented aspiration of tissue from catheter 110 into syringe 120, the barrel 122 of syringe 120 being connected to catheter 110 via tissue trap 112.

After latching mechanism 126 has been released from proximal end 125 of plunger 121, allowing spring 123 to expand, plunger 121 then becomes a depressible plunger. I.e., the plunger may now be depressed by application of, for example, an operator's thumb to the proximal end 125 of plunger 121. Depressing plunger 121 expels aspirated tissue from the lumen of catheter 110 as illustrated in FIG. 7, which shows the device being held stably over a specimen container 150 with the operator's thumb depressing spring-loaded plunger 121 to expel collected sample 140 from side hole 111 in a controlled fashion. Thus, there is no need to disassemble the syringe from the catheter to obtain the aspirated tissue, nor is any reconfiguration of the device required, the device being automatically configured for sample delivery into a specimen container.

Figure 4:
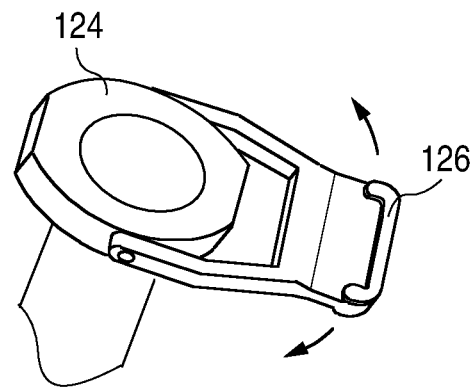
FIG. 4 is an enlarged view of a portion of the biopsy device of FIGS. 1 and 2, the enlarged view showing a movable latching mechanism attached to a syringe barrel.
Figure 5:
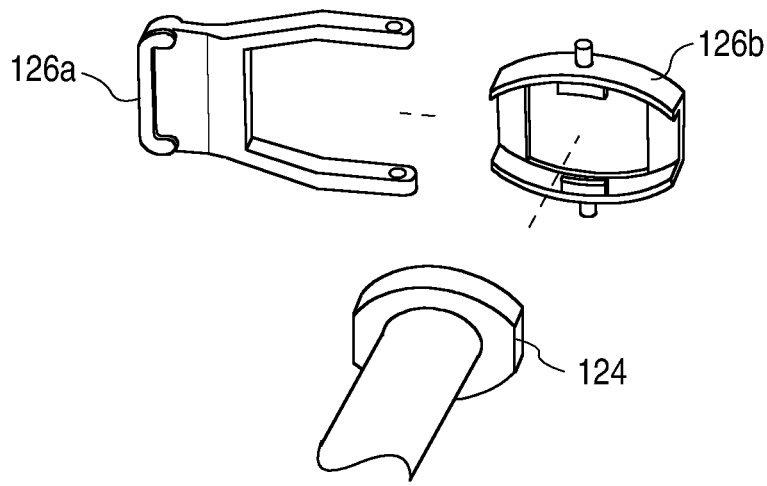
FIG. 5 is an enlarged view of a portion of the biopsy device of FIGS. 1 and 2, the enlarged view showing another movable latching mechanism that is fully detachable from the syringe barrel.

FIG. 4 illustrates one embodiment of latching mechanism 126 in which the latching mechanism is a single piece that is movably attached to one or more edges of flange 124 of barrel 122. Flange 124 is illustrated in the figures as a substantially circular or oval ring at the proximal end of barrel 122 but could, alternatively, be one or more tabs extending outward from the body of barrel 122 or even a substantially straight proximal portion of barrel 122. FIG. 5 illustrates another embodiment of latching mechanism 126 in which the latching mechanism is fully detachable from syringe 120 and comprises two segments, the first segment 126a being sized and structured to be removably placed over plunger proximal end 125 to maintain spring 123 in a compressed state, and the second segment 126b being a cap-like structure that may be fitted over flange 124 or the flange of a standard syringe. In both embodiments, the latching mechanism is movably attached to syringe 120 to permit not only easy release of the latching mechanism from the proximal end 125 of plunger 121, but also reattachment of the latching mechanism to plunger end 125 when plunger 121 is depressed. Thus, latching mechanism 126 facilitates plunger 121 being returned to a spring-loaded state after expulsion of an aspirated sample from the biopsy device (i.e., providing a mechanism for re-latching the spring-loaded plunger), preparing the device for repeated use if desired. Note that the location and design of the latching mechanism allows the biopsy device to be operated with one hand. In each of the embodiments illustrated in FIGS. 1-7, the latching mechanisms 126, 126a are coupled to substantially diametrically opposing locations on barrel 122.

Yet another aspect of the present invention is a method of performing a biopsy procedure. In the method, an aspiration biopsy device is provided, the device comprising a catheter having a distally placed tissue acquisition side hole and a proximally attached syringe having a spring-loaded plunger and a latching mechanism. The device may be a device such as has been described above and illustrated in FIGS. 1-7.

A distal portion of the device is inserted into a body cavity. For example, all or a portion of catheter 110 may be inserted into a uterine cavity 130 as seen in FIG. 2. Once the device portion is in place within the body cavity, the latching mechanism is manipulated to release the spring-loaded plunger, thereby automatically producing aspiration suction within the syringe that is communicated to the catheter. The device portion is moved in and out with a twirling motion, thereby collecting a biopsy sample via the distally placed tissue acquisition side hole (e.g., side hole 111). Passage of the biopsy sample from the catheter into the syringe may be prevented by the inclusion within a proximal portion of the catheter of a tissue trap comprising a filter or a pin-hole channel.

After collecting the biopsy sample, the device portion is removed from the body cavity. The device may then be held over a specimen container, and the spring-loaded plunger may be depressed, e.g., using a thumb, to expel the sample into the specimen container as, for example, illustrated in FIG. 7. After the sample has been expelled into the specimen container, the latching mechanism may be manipulated to restrain the spring-loaded plunger (i.e., to return the spring-loaded plunger to its starting position and status), thereby preparing the device for repeated use if desired.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. An automatically aspirated biopsy device comprising:
an endometrial biopsy catheter having a distal end and a proximal end;
an aspiration syringe having a first distal end and a first proximal end, the syringe including an outer barrel and a plunger, having a plunger proximal end, the plunger disposed within the barrel and reciprocably movable therewithin between a depressed position and a retracted position, wherein the proximal end of the catheter is coupled to a second distal end of the outer barrel;
a biasing member disposed between the barrel and the plunger, the biasing member biasing the plunger toward the retracted position;
a releasable latching mechanism coupled to substantially diametrically opposing locations on the barrel, the latching mechanism including first and second legs pivotably coupled on substantially opposite sides of the barrel, coupled together at proximal leg ends thereof via a tab, wherein the tab is configured to extend across, and bear against, the plunger proximal end when the plunger is in the retracted position, such that the latching mechanism and the biasing member exert substantially laterally symmetrical opposing forces upon the plunger, the latching mechanism configured to releasably retain the plunger in the depressed position, whereupon release of the latching mechanism, the biasing member prompts the plunger to move toward the retracted position.

2. The biopsy device according to claim 1, wherein the catheter further comprises a rounded distal end with at least one tissue acquisition side hole.

3. The biopsy device according to claim 1, wherein the biasing member comprises a coil spring coupled at a first end to a second proximal end of the barrel and at a second end to the plunger proximal end.

4. The biopsy device according to claim 1, wherein the barrel further comprises:
a tissue trap sized to prevent undesired tissue material from being drawn into the barrel during movement of the plunger from the depressed position to the retracted position.

* * * * *